(12) United States Patent
Wang et al.

(10) Patent No.: US 7,704,687 B2
(45) Date of Patent: Apr. 27, 2010

(54) DIGITAL KARYOTYPING

(75) Inventors: Tian-Li Wang, Baltimore, MD (US);
Victor Velculescu, Dayton, MD (US);
Kenneth Kinzler, Bel Air, MD (US);
Bert Vogelstein, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1063 days.

(21) Appl. No.: 10/705,874

(22) Filed: Nov. 13, 2003

(65) Prior Publication Data

US 2004/0096892 A1  May 20, 2004

Related U.S. Application Data

(60) Provisional application No. 60/426,406, filed on Nov. 15, 2002.

(51) Int. Cl.
*C12Q 1/68* (2006.01)
*G06F 19/00* (2006.01)
*G01N 33/48* (2006.01)
*C40B 40/08* (2006.01)
*C12P 19/34* (2006.01)

(52) U.S. Cl. .............................. 435/6; 702/19; 702/20; 435/91.2

(58) Field of Classification Search ........................ None
See application file for complete search history.

(56) References Cited

U.S. PATENT DOCUMENTS

| | | | | |
|---|---|---|---|---|
| 5,200,336 A | * | 4/1993 | Kong et al. | 435/199 |
| 5,391,480 A | * | 2/1995 | Davis et al. | 435/6 |
| 5,663,048 A | * | 9/1997 | Winkfein et al. | 435/6 |
| 5,695,937 A | | 12/1997 | Kinzler et al. | |
| 5,981,190 A | | 11/1999 | Israel | |
| 6,498,013 B1 | | 12/2002 | Velculescu et al. | |
| 2002/0048767 A1 | * | 4/2002 | Bensimon et al. | 435/6 |
| 2002/0147549 A1 | * | 10/2002 | Yoshida et al. | 702/20 |
| 2003/0124584 A1 | * | 7/2003 | Mohammed | 435/6 |
| 2003/0186251 A1 | | 10/2003 | Dunn et al. | |
| 2004/0219580 A1 | | 11/2004 | Dunn et al. | |

FOREIGN PATENT DOCUMENTS

WO    WO 0202805 A2  *  1/2002

OTHER PUBLICATIONS

New England Biolabs Technical online reference (www.neb.com/nebecomm/tech_reference/restriction_enzymes/overview.asp) pp. 1-4, 2007.*
Dunn, J. et al., "Genomic Signature Tags (GSTs)" A System for Profiling Genomic DNA, *Genome Research*, pp. (2002) 12:1756-1765.
Wang, T. et al., "Digital karyotyping," *PNAS*, (Dec. 10, 2002), vol. 99, No. 25, pp. 16156-16161.
Kallioniemi, A. et al., "Comparative Genomic Hybridization for Molecular Cytogenetic Analysis of Solid Tumors" *Science*, vol. 258 (Oct. 30, 1992), pp. 818-821.

* cited by examiner

*Primary Examiner*—Nancy Vogel
*Assistant Examiner*—Catherine Hibbert
(74) *Attorney, Agent, or Firm*—Banner & Witcoff, Ltd.

(57) ABSTRACT

Alterations in the genetic content of a cell underlie many human diseases, including cancers. A method called Digital Karyotyping provides quantitative analysis of DNA copy number at high resolution. This approach involves the isolation and enumeration of short sequence tags from specific genomic loci. Analysis of human cancer cells using this method identified gross chromosomal changes as well as amplifications and deletions, including regions not previously known to be altered. Foreign DNA sequences not present in the normal human genome could also be readily identified. Digital Karyotyping provides a broadly applicable means for systematic detection of DNA copy number changes on a genomic scale.

27 Claims, 5 Drawing Sheets

US 7,704,687 B2

DIGITAL KARYOTYPING

This application claims the benefit of provisional application Ser. No. 60/426,406 filed Nov. 15, 2002, the contents of which are expressly incorporated herein.

The work underlying this invention was supported in part by the U.S. government. Thus the U.S. government retains certain rights in the invention according to the provisions of grant nos. CA 43460, CA 57345, CA 62924 of the National Institutes of Health.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The invention relates to the field of genetics. In particular, it relates to the determination of karyotypes of genomes of individuals.

BACKGROUND OF THE INVENTION

Somatic and hereditary variations in gene copy number can lead to profound abnormalities at the cellular and organismal levels. In human cancer, chromosomal changes, including deletion of tumor suppressor genes and amplification of oncogenes, are hallmarks of neoplasia (1). Single copy changes in specific chromosomes or smaller regions can result in a number of developmental disorders, including Down, Prader Willi, Angelman, and cri du chat syndromes (2). Current methods for analysis of cellular genetic content include comparative genomic hybridization (CGH) (3), representational difference analysis (4), spectral karyotyping/M-FISH (5, 6), microarrays (7-10), and traditional cytogenetics. Such techniques have aided in the identification of genetic aberrations in human malignancies and other diseases (11-14). However, methods employing metaphase chromosomes have a limited mapping resolution (~20 Mb) (15) and therefore cannot be used to detect smaller alterations. Recent implementation of comparative genomic hybridization to microarrays containing genomic or transcript DNA sequences provide improved resolution, but are currently limited by the number of sequences that can be assessed (16) or by the difficulty of detecting certain alterations (9). There is a continuing need in the art for methods of analyzing and comparing genomes.

BRIEF SUMMARY OF THE INVENTION

In a first embodiment a method is provided for karyotyping a genome of a test eukaryotic cell. A population of sequence tags is generated from defined portions of the genome of the test eukaryotic cell. The portions are defined by one or two restriction endonuclease recognition sites. The sequence tags in the population are enumerated to determine the number of individual sequence tags present in the population. The number of a plurality of sequence tags in the population is compared to the number of the plurality of sequence tags determined for a genome of a reference cell. The plurality of sequence tags are within a window of sequence tags which are calculated to be contiguous in the genome of the species of the eukaryotic cell. A difference in the number of the plurality of sequence tags within the window present in the population from the number determined for a reference eukaryotic cell indicates a karyotypic difference between the test eukaryotic cell and the reference eukaryotic cell.

According to a second embodiment of the invention, a dimer is provided. The dimer comprises two distinct sequence tags from defined portions of the genome of a eukaryotic cell. The portions are defined by one or two restriction endonuclease recognition sites. Each of said sequence tags consists of a fixed number of nucleotides of one of said defined portions of the genome. The fixed number of nucleotides extend from one of said restriction endonuclease recognition sites.

According to a third embodiment of the invention, a concatamer of dimers is provided. The dimers comprise two distinct sequence tags from defined portions of the genome of a eukaryotic cell. The portions are defined by one or two restriction endonuclease recognition sites. Each of said sequence tags consists of a fixed number of nucleotides of one of said defined portions of the genome. The fixed number of nucleotides extend from one of the restriction endonuclease recognition sites.

According to a fourth embodiment of the invention a method of karyotyping a genome of a test eukaryotic cell is provided. A population of sequence tags is generated from defined portions of the genome of the test eukaryotic cell. The portions are defined by one or two restriction endonuclease recognition sites. The sequence tags in the population are enumerated to determine the number of individual sequence tags present in the population. The number of a plurality of sequence tags in the population is compared to the number of said plurality of sequence tags calculated to be present in the genome of the species of the eukaryotic cell. The plurality of sequence tags are within a window of sequence tags which are calculated to be contiguous in the genome of the species of the eukaryotic cell. A difference in the number of the plurality of sequence tags within the window present in the population from the number calculated to be present in the genome of the eukaryotic cell indicates a karyotypic abnormality.

BRIEF DESCRIPTION OF THE DRAWINGS

(FIG. 3A) Amplification on chromosome 7. Top panel represent bitmap viewer with the region containing the alteration encircled. The bitmap viewer is comprised of ~39,000 pixels representing tag density values at the chromosomal position of each virtual tag on chromosome 7, determined from sliding windows of 50 virtual tags. Yellow pixels indicate tag densities corresponding to copy numbers <110 while black pixels correspond to copy number ≧110. Middle panel represents an enlarged view of the region of alteration. The lower panel indicates a graphical representation of the amplified region with values on the Y-axis indicating genome copies per haploid genome and values on the X-axis representing position along the chromosome in Mb. (FIG. 3B) Homozygous deletion on chromosome 5. Top, middle and lower panels are similar to those for (FIG. 3A) except that the bitmap viewer for chromosome 5 contains ~43,000 pixels, tag density values were calculated in sliding windows of 150 virtual tags, and yellow pixels indicate copy numbers >0.1 while black pixels indicate copy numbers ≦0.1. Bottom panel represents detailed analysis of the region containing the homozygous deletion in DiFi and Co52. For each sample, white dots indicate markers that were retained, while black dots indicate markers that were homozygously deleted. PCR primers for each marker are listed in Table 4

DETAILED DESCRIPTION OF THE INVENTION

Figure 1:
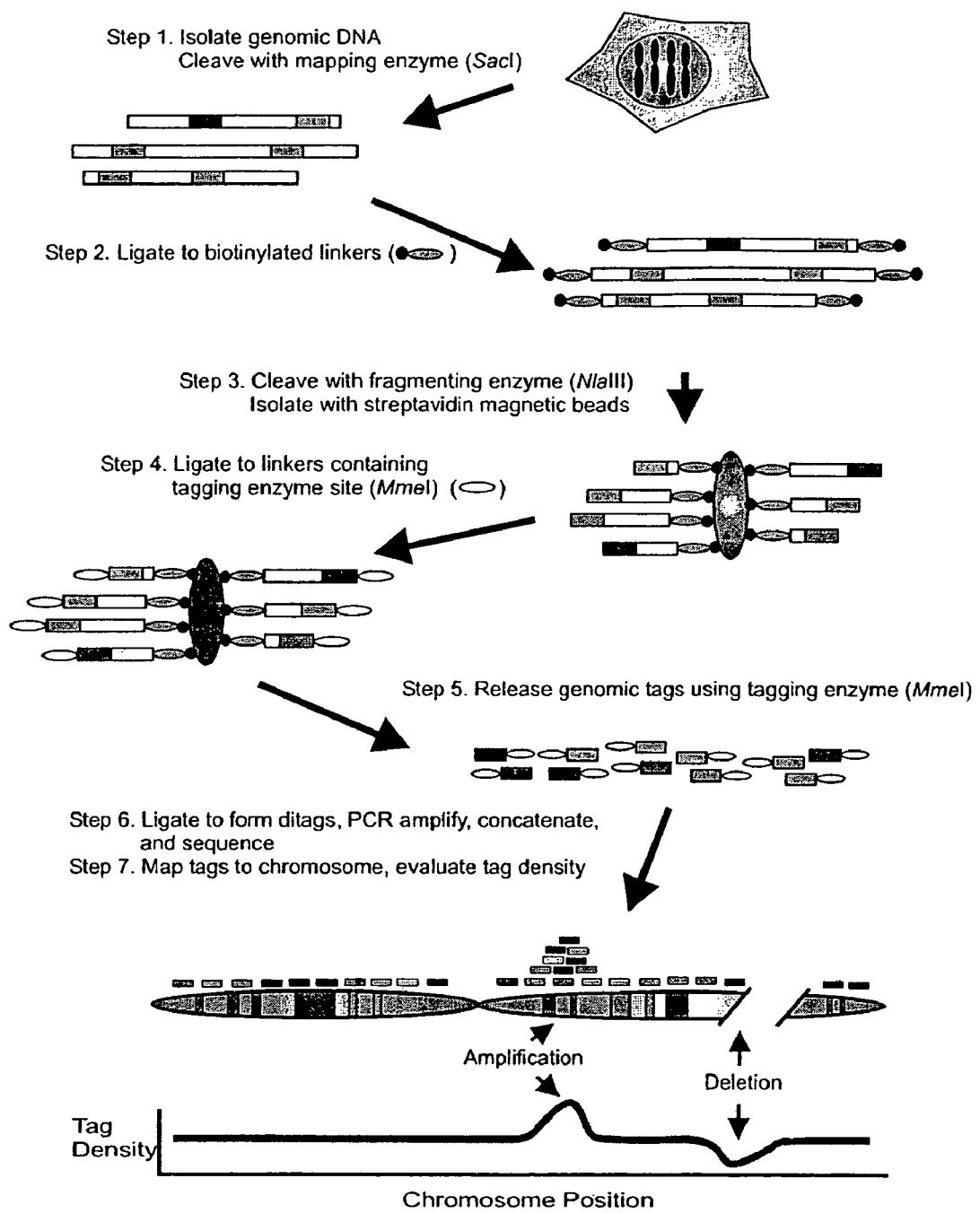
FIG. 1. Schematic of Digital Karyotyping approach. Colored boxes represent genomic tags. Small ovals represent linkers. Large blue ovals represent streptavidin-coated magnetic beads. This figure is described in more detail below.

It is a discovery of the present inventors that the genome of an organism can be sampled in groups of small pieces to determine karyotypic properties of an organism using a systematic and quantitative method. Changes in copy number of portions of the genome can be determined on a genomic scale. Such changes include gain or loss of whole chromosomes or chromosome arms, amplifications and deletions of regions of the genome, as well as insertions of foreign DNA. Rearrangements, such as translocations and inversions, would typically not be detected by the method.

Our data demonstrate that the method, called Digital Karyotyping, can accurately identify regions whose copy number is abnormal, even in complex genomes such as that of the human. Whole chromosome changes, gains or losses of chromosomal arms, and interstitial amplifications or deletions can be detected. Moreover, the method permits the identification of specific amplifications and deletions that had not been previously described by comparative genomic hybridization (CGH) or other methods in any human cancer. These analyses suggest that a potentially large number of undiscovered copy number alterations exist in cancer genomes and that many of these could be detected through Digital Karyotyping.

Like all genome-wide analyses, Digital Karyotyping has limitations. First, the ability to measure tag densities over entire chromosomes depends on the accuracy and completeness of the genome sequence. Fortunately, over 94% of the human genome is available in draft form, and 95% of the sequence is expected to be in a finished state by 2003. Second, a small number of areas of the genome are expected to have a lower density of mapping enzyme restriction sites and be incompletely evaluated by our approach. We estimate that less than 5% of the genome would be incompletely analyzed using the parameters employed in the current study. Moreover, this problem could be overcome through the use of different mapping and fragmenting enzymes. Finally, Digital Karyotyping cannot generally detect very small regions, on the order of several thousand base pairs or less, that are amplified or deleted.

Nevertheless, it is clear from our analyses that Digital Karyotyping provides a heretofore unavailable picture of the DNA landscape of a cell. The approach should be immediately applicable to the analysis of human cancers, wherein identification of homozygous deletions and amplifications has historically revealed genes important in tumor initiation and progression. In addition, one can envisage a variety of other applications for this technique. First, the approach could be used to identify previously undiscovered alterations in hereditary disorders. A potentially large number of such diseases are thought to be due to deletions or duplications too small to be detected by conventional approaches. These may be detectable with Digital Karyotyping even in the absence of any linkage or other positional information. Second, use of mapping enzymes that are sensitive to DNA methylation (e.g. NotI) could be employed to catalog genome-wide methylation changes in cancer or diseases thought to be affected by genomic imprinting. Third, the approach could be as easily applied to the genomes of other organisms to search for genetic alterations responsible for specific phenotypes, or to identify evolutionary differences between related species. Moreover, as the genome sequences of increasing numbers of microorganisms and viruses become available, the approach can be used to identify the presence of pathogenic DNA in infectious or neoplastic states.

Populations of sequence tags are generated from defined portions of the genome. The portions are defined by one or two restriction endonuclease recognition sites. Preferably the recognition sites are located in a fixed position within the defined portions of the genome. In one embodiment three different restriction endonucleases are used to generate sequence tags. In this embodiment, the restriction endonucleases used to generate the tags can be termed mapping (first), fragmenting (second), and tagging restriction endonuclease. The defined portions extend from the fragmenting (second) restriction endonuclease site to the closest mapping (first) restriction endonuclease site. The sequence tags derived from these defined portions are generated by cleavage with a tagging enzyme. The closest nucleotides adjacent to the fragmenting (second) restriction endonuclease comprise the sequence tags. The number of nucleotides is typically a fixed number (defined here to include a range of numbers) which is a function of the properties of the tagging (third) restriction endonuclease. For example, using MmeI the fixed number is 20, 21 or 22. Other Type IIS restriction endonucleases cleave at different distances from their recognition sequences. Other Type IIS restriction endonucleases which can be used include BbvI, BbvII, BinI, FokI, HgaI, HphI, MboII, MnlI, SfaNI, TaqII, TthlllII , BsmFI, and FokI. See Szybalski, W., Gene, 40:169, 1985. Other similar enzymes will be known to those of skill in the art (see, Current Protocols in Molecular Biology, supra). Restriction endonucleases with desirable properties can be artificially evolved, i.e., subjected to selection and screening, to obtain an enzyme which is useful as a tagging enzyme. Desirable enzymes cleave at least 18-21 nucleotides distant from their recognition sites. Artificial restriction endonucleases can also be used. Such endonucleases are made by protein engineering. For example, the endonuclease FokI has been engineered by insertions so that it cleaves one nucleotide further away from its recognition site on both strands of the DNA substrates. See Li and Chandrasegaran, *Proc. Nat. Acad. Sciences USA* 90:2764-8, 1993. Such techniques can be applied to generate restriction endonucleases with desirable recognition sequences and desirable distances from recognition site to cleavage site.

In an alternative embodiment a single restriction endonuclease can define a defined portion of the genome. A fixed number of nucleotides on one or both sides of the restriction endonuclease recognition site then forms the sequence tags. For example, the restriction endonuclease BcgI can be used to provide a 36 bp fragment. The 12 bp recognition site (having 6 degenerate positions) lies in the middle of a fragment; 12 bp flank the site on either side. Other similar enzymes which can be used in this embodiment include BplI and BsaXI. Preferably the enzyme used releases a fragment having a sum of at least 18 or 20 nucleotides flanking its recognition sequence.

Enumeration of sequence tags generated is performed by determining the identity of the sequence tags and recording the number of occurrences of each such tag or of genomically clustered tags. Preferably the determination of identity of the tags is done by automated nucleotide sequence determination and the recording is done by computer. Other methods for identifying and recording tags can be used, as is convenient and efficient to the practitioner. According to one embodiment of the invention sequence tags are ligated together to form a concatenate and the concatenates are cloned and seqeunces. In a preferred embodiment the sequence tags are dimerized prior to formation of the concatenate. The sequence tags can be amplified as single tags or as dimers prior to concatenation.

A feature of the data analysis which enables the efficient practice of the method is the use of windows. These are groups of sequence tags which are genomically clustered. Virtual tags can be extracted from the genomic data for the species being tested. The virtual tags are associated with locations in the genome. Groups of adjacent virtual tags which are clustered in the genome are used to form a window for analysis of actual experimental tags. The term adjacent or contiguous as used herein to describe tags does not imply that the nucleotides of one tag are contiguous with the nucleotides of another tag, but rather that the tags are clustered in the same areas of the genome. Because of the way that sequence tags are generated, they only sample the genome; they do not saturate the genome. Thus, for example, a window can comprise sequence tags that map within about 40 kb, about 200 kb, about 600 kb, or about 4 Mb. Typically such windows comprise from 10 to 1000 sequence tags. Use of windows such as these permits the genome to be sampled rather than comprehensively analyzed. Thus, far less than 100% of the sequence tags must be counted to obtain useful information. In fact, less than 50%, less than 33%, less than 25%, less than 20%, even less than 15% of the sequence tags calculated to be present in the genome of the eukaryotic cell need be enumerated to obtain useful data. The karyotypic analysis can be used inter alia to compare a cancer cell to a normal cell, thereby identifying regions of genomic change involved in cancer. The karyotypic analysis can be used to identify genes involved in hereditary disorders. The karyotypic analysis can be used to identify genetic material in a eukaryotic cell derived from an infectious agent.

Changes in amount of particular regions of the genome can identify aneuploidy if (a) sequence tags of one or more autosomes are determined to be present in the test eukaryotic cell relative to the reference eukaryotic cell at a ratio of 3 or greater or less than 1.5; or (b) sequence tags of one or more sex chromosomes in a male are determined to be present in the test eukaryotic cell relative to the reference eukaryotic cell at a ratio of 1.5 or greater or less than 0.7; or (c) sequence tags of X chromosomes in a female are determined to be present in the test eukaryotic cell relative to the reference eukaryotic cell at a ratio of 3 or greater or less than 1.5, or relative to a reference female eukaryotic cell at a ratio of 1.5 or greater or less than 0.7. Similarly, such changes can be measured with reference to nucleotide sequence data for the genome of a particular species.

Preferably the method of the present invention employs the formation of dimers of sequence tags. Such dimers permit the elimination of certain types of bias, for example that which might be introduced during amplification of tags. Typically dimers which do not comprise two distinct tags are excluded from analysis. Two sequence tags which form a dimer are desirably joined end-to-end at the ends distal to the second restriction endonuclease (fragmenting) site. Such distal ends are typically formed by the action of the tagging enzyme, i.e., the third restriction endonuclease. Preferably the distal ends are sticky ends. All or part of the oligonucleotide linkers can remain as part of the dimers and can remain as part of the concatenates of dimers as well. However, the linkers are preferably cleaved prior to the concatenation.

EXAMPLES

Example 1

Principles of Digital Karyotyping

These concepts are practically incorporated into Digital Karyotyping of human DNA as described in FIG. 1. Genomic DNA is cleaved with a restriction endonuclease (mapping enzyme) that is predicted to cleave genomic DNA into several hundred thousand pieces, each on average <10 kb in size (Step 1). A variety of different endonucleases can be used for this purpose, depending on the resolution desired. In the current study, we have used SacI, with a 6-bp recognition sequence predicted to preferentially cleave near or within transcribed genes. Biotinylated linkers are ligated to the DNA molecules (Step 2) and then digested with a second endonuclease (fragmenting enzyme) that recognizes 4-bp sequences (Step 3). As there are on average 16 fragmenting enzyme sites between every two mapping enzyme sites ($4^6/4^4$), the majority of DNA molecules in the template are expected to be cleaved by both enzymes and thereby be available for subsequent steps. DNA fragments containing biotinylated linkers are separated from the remaining fragments using streptavidin-coated magnetic beads (Step 3). New linkers, containing a 5-bp site recognized by MmeI, a type IIS restriction endonuclease (18), are ligated to the captured DNA (Step 4). The captured fragments are cleaved by MmeI, releasing 21 bp tags (Step 5). Each tag is thus derived from the sequence adjacent to the fragmenting enzyme site that is closest to the nearest mapping enzyme site. Isolated tags are self-ligated to form ditags, PCR amplified en masse, concatenated, cloned, and sequenced (Step 6). As described for SAGE (17), formation of ditags provides a robust method to eliminate potential PCR induced bias during the procedure. Current automated sequencing technologies identify up to 30 tags per concatamer clone, allowing for analysis of ~100,000 tags per day using a single 384 capillary sequencing apparatus. Finally, tags are computationally extracted from sequence data, matched to precise chromosomal locations, and tag densities are evaluated over moving windows to detect abnormalities in DNA sequence content (Step 7).

The sensitivity and specificity of Digital Karyotyping in detecting genome-wide changes was expected to depend on several factors. First, the combination of mapping and fragmenting enzymes determines the minimum size of the alterations that can be identified. For example, use of SacI and NlaIII as mapping and fragmenting enzymes, respectively, was predicted to result in a total of 730,862 virtual tags (defined as all possible tags that could theoretically be obtained from the human genome). These virtual tags were spaced at an average of 3,864 bp, with 95% separated by 4 bp to 46 kb. Practically, this resolution is limited by the number of tags actually sampled in a given experiment and the type of alteration present (Table 1). Monte Carlo simulations confirmed the intuitive concept that fewer tags are needed to detect high copy number amplifications than homozygous deletions or low copy number changes in similar sized regions (Table 1). Such simulations were used to predict the size of alterations that could be reliably detected given a fixed number of experimentally sampled tags. For example, analysis of 100,000 tags would be expected to reliably detect a 10-fold amplification ≧100 kb, homozygous deletions ≧600 kb, or a single gain or loss of regions ≧4 Mb in size in a diploid genome (Table 1).

Example 2

Analysis of Whole Chromosomes

We characterized 210,245 genomic tags from lymphoblastoid cells of a normal individual (NLB) and 171,795 genomic tags from the colorectal cancer cell line (DiFi) using the mapping and fragmenting enzymes described above. After filtering to remove tags that were within repeated sequences or were not present in the human genome (see Materials and Methods), we recovered a total of 111,245 and 107,515 filtered tags from the NLB and DiFi libraries, respectively. Tags were ordered along each chromosome, and average chromosomal tag densities, defined as the number of detected tags divided by the number of virtual tags present in a given chromosome, were evaluated (Table 2). Analysis of the NLB data showed that the average tag densities for each autosomal chromosome was similar, ~0.16+/−0.04. The small variations in tag densities were likely due to incomplete filtering of tags matching repeated sequences that were not currently represented in the genome databases. The X and Y chromosomes had average densities about half this level, 0.073 and 0.068, respectively, consistent with the normal male karyotype of these cells. Analysis of the DiFi data revealed a much wider variation in tag densities, ranging from 0.089 to 0.27 for autosomal chromosomes. In agreement with the origin of these tumor cells from a female patient (20), the tag density of the Y chromosome was 0.00. Estimates of chromosome number using observed tag densities normalized to densities from lymphoblastoid cells suggested a highly aneuploid genetic content, with ≦1.5 copies of chromosome 1, 4, 5, 8, 17, 21 and 22, and ≧3 copies of chromosome 7, 13 and 20 per diploid genome. These observations were consistent with CGH analyses (see below) and the previously reported karyotype of DiFi cells (20).

TABLE 1

Theoretical detection of copy number alterations using Digital Karyotyping*

| Size of Alteration[+] | | Amplification Copy number = 10 | | Homozygous deletion Copy number = 0 | | Heterozygous loss Copy number = 1 | | Subchromosomal gain Copy number = 3 | |
|---|---|---|---|---|---|---|---|---|---|
| # bp | # virtual tags | 100,000 | 1,000,000 | 100,000 | 1,000,000 | 100,000 | 1,000,000 | 100,000 | 1,000,000 |
| 100,000 | 30 | 100% | 100% | 0.06% | 100% | 0.008% | 0.02% | 0.006% | 0.08% |
| 200,000 | 50 | 100% | 100% | 1% | 100% | 0.01% | 3% | 0.01% | 0.7% |
| 600,000 | 150 | 100% | 100% | 96% | 100% | 0.07% | 100% | 0.05% | 100% |
| 2,000,000 | 500 | 100% | 100% | 100% | 100% | 11% | 100% | 3% | 100% |
| 4,000,000 | 1000 | 100% | 100% | 100% | 100% | 99% | 100% | 97% | 100% |

*Copy number alteration refers to the gain or loss of chromosomal regions in the context of the normal diploid genome, where the normal copy number is 2. The limiting feature of these analyses was not sensitivity for detecting the alteration, as this was high in every case shown (>99% for amplifications and homozygous deletions and >92% for heterozygous losses or subchromosomal gains). What was of more concern was the positive predictive value (PPV), that is, the probability that a detected mutation represents a real mutation. PPVs were calculated from 100 simulated genomes, using 100,000 or 1,000,000 filtered tags, and shown in the table as percents.
[+]Size of alteration refers to the approximate size of the genomic alteration assuming an average of 3864 bp between virtual tags.

TABLE 2

Chromosome number analysis

| Chromosome | Virtual Tags | NLB Observed tags | NLB Tag density | DiFi Observed tags | DiFi Tag density | Chromosome content* |
|---|---|---|---|---|---|---|
| 1 | 61,694 | 10,090 | 0.16 | 6,991 | 0.11 | *1.4* |
| 2 | 61,944 | 9,422 | 0.15 | 9,545 | 0.15 | 2.0 |
| 3 | 46,337 | 6,732 | 0.15 | 7,379 | 0.16 | 2.2 |
| 4 | 41,296 | 5,581 | 0.14 | 3,666 | 0.089 | *1.3* |
| 5 | 43,186 | 6,216 | 0.14 | 4,136 | 0.10 | *1.3* |
| 6 | 41,633 | 6,120 | 0.15 | 7,291 | 0.18 | 2.4 |
| 7 | 38,928 | 5,836 | 0.15 | 9,875 | 0.25 | 3.4 |
| 8 | 35,033 | 5,009 | 0.14 | 3,260 | 0.093 | *1.3* |
| 9 | 30,357 | 4,909 | 0.16 | 4,861 | 0.16 | 2.0 |
| 10 | 37,320 | 6,045 | 0.16 | 4,865 | 0.13 | 1.6 |
| 11 | 37,868 | 6,081 | 0.16 | 5,432 | 0.14 | 1.8 |
| 12 | 30,692 | 4,631 | 0.15 | 4,056 | 0.13 | 1.8 |
| 13 | 22,313 | 3,012 | 0.13 | 5,197 | 0.23 | 3.5 |
| 14 | 23,378 | 3,658 | 0.16 | 3,171 | 0.14 | 1.7 |
| 15 | 22,409 | 3,581 | 0.16 | 4,159 | 0.19 | 2.3 |
| 16 | 23,028 | 4,119 | 0.18 | 3,201 | 0.14 | 1.6 |
| 17 | 22,978 | 4,298 | 0.19 | 3,145 | 0.14 | *1.5* |
| 18 | 18,431 | 2,712 | 0.15 | 2,389 | 0.13 | 1.8 |
| 19 | 16,544 | 3,271 | 0.20 | 3,589 | 0.22 | 2.2 |
| 20 | 20,585 | 3,573 | 0.17 | 5,460 | 0.27 | 3.1 |
| 21 | 9,245 | 1,465 | 0.16 | 1,036 | 0.11 | *1.4* |
| 22 | 12,579 | 2,476 | 0.20 | 1,655 | 0.13 | *1.3* |
| X | 30,737 | 2,249 | 0.073 | 3,147 | 0.10 | 1.4 |
| Y | 2,347 | 159 | 0.068 | 9 | 0.00 | 0.06 |
| Total | 730,862 | 111,245 | 0.15 | 107,515 | 0.15 | 2.0 |

*DiFi chromosomal content is calculated for autosomal chromosomes as two times the ratio of DiFi tag densities to corresponding NLB tag densities, and for the X chromosome as the ratio of DIFI tag density to NLB tag density. Values in bold represent autosomal chromosome content ≧3 while values in italics represent autosomal chromosome content <1.5.

Example 3

Analysis of Chromosomal Arms

Figure 2:
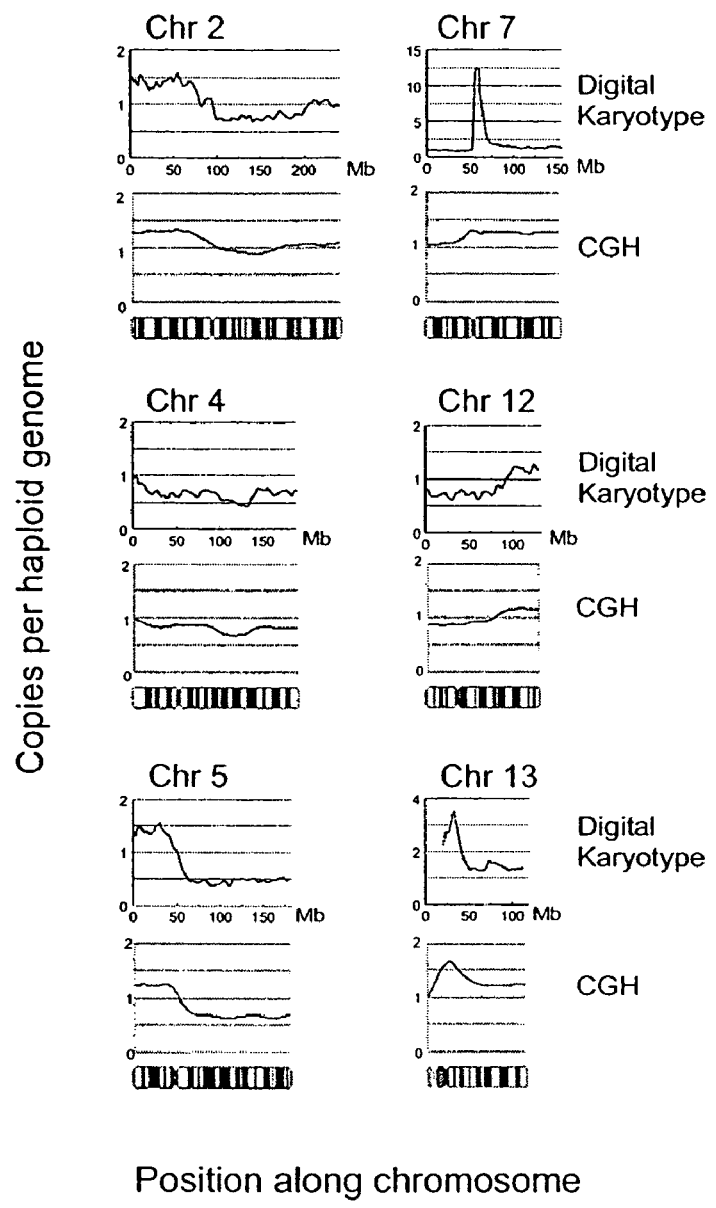
FIG. 2. Low resolution tag density maps reveal many sub-chromosomal changes. The top graph corresponds to the Digital Karyotype, while the lower graph represents CGH analysis. An ideogram of each normal chromosome is present under each set of graphs. For all graphs, values on the Y-axis indicate genome copies per haploid genome, and values on the X-axis represent position along chromosome (Mb for Digital Karyotype, and chromosome bands for CGH). Digital Karyotype values represent exponentially smoothed ratios of DiFi tag densities, using a sliding window of 1000 virtual tags normalized to the NLB genome. Chromosomal areas lacking Digital Karyotype values correspond to unsequenced portions of the genome, including heterochromatic regions. Note that using a window of 1000 virtual tags does not permit accurate identification alterations less than ~4 Mb, such as amplifications and homozygous deletions, and smaller windows need to be employed to accurately identify these lesions (see FIG. 3 for example).
Figure 5:
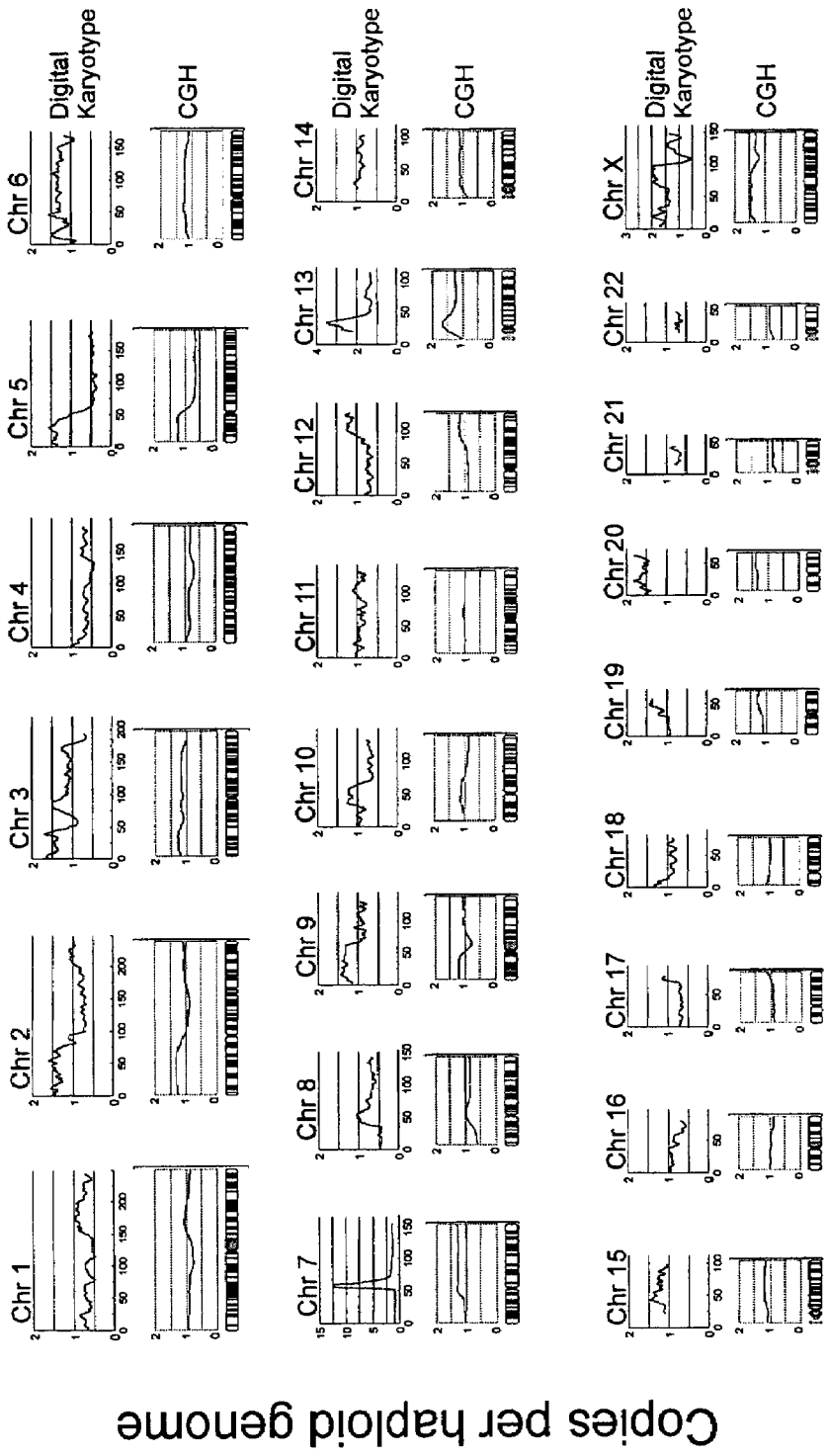
FIG. 5. Low resolution tag density maps of the DiFi tumor genome. For each chromosome, the top graph corresponds to the Digital Karyotype while the lower graph represents CGH analysis. An ideogram of each chromosome is depicted under each set of graphs. For all graphs, values on the Y-axis indicate genome copies per haploid genome, and values on the X-axis represent position along chromosome (Mb for Digital Karyotypes, and chromosome bands for CGH). Digital Karyotype values represent exponentially smoothed ratios of DiFi tag densities, using a sliding window of 1000 virtual tags normalized to the NLB genome. Chromosomal areas lacking Digital Karyotype values correspond to unsequenced portions of the genome, including heterochromatic regions.

We next evaluated the ability of Digital Karyotyping to detect subchromosomal changes, particularly gains and losses of chromosomal arms. Tag densities were analyzed along each chromosome using sliding windows containing 1000 virtual tags (~4 Mb), as windows of this size were predicted to reliably detect such alterations (Table 1). For the NLB sample, tag density maps showed uniform content along each chromosome, with small variations (<1.5 fold) present over localized regions, presumably due to overrepresentation of tags matching repeated sequences (data not shown). In contrast, the DiFi tag density map (normalized to the NLB data) revealed widespread changes, including apparent losses in large regions of 5q, 8p and 10q, and gains of 2p, 7q, 9p, 12q, 13q, and 19q (FIG. 2 and FIG. 5). These changes included regions of known tumor suppressor genes (21) and other areas commonly altered in colorectal cancer (11, 12, 22). These alterations were confirmed by chromosomal CGH analyses, which revealed aberrations that were largely consistent with Digital Karyotype analyses in both location and amplitude (FIG. 2 and FIG. 5).

Example 4

Analysis of Amplifications

Figure 3:
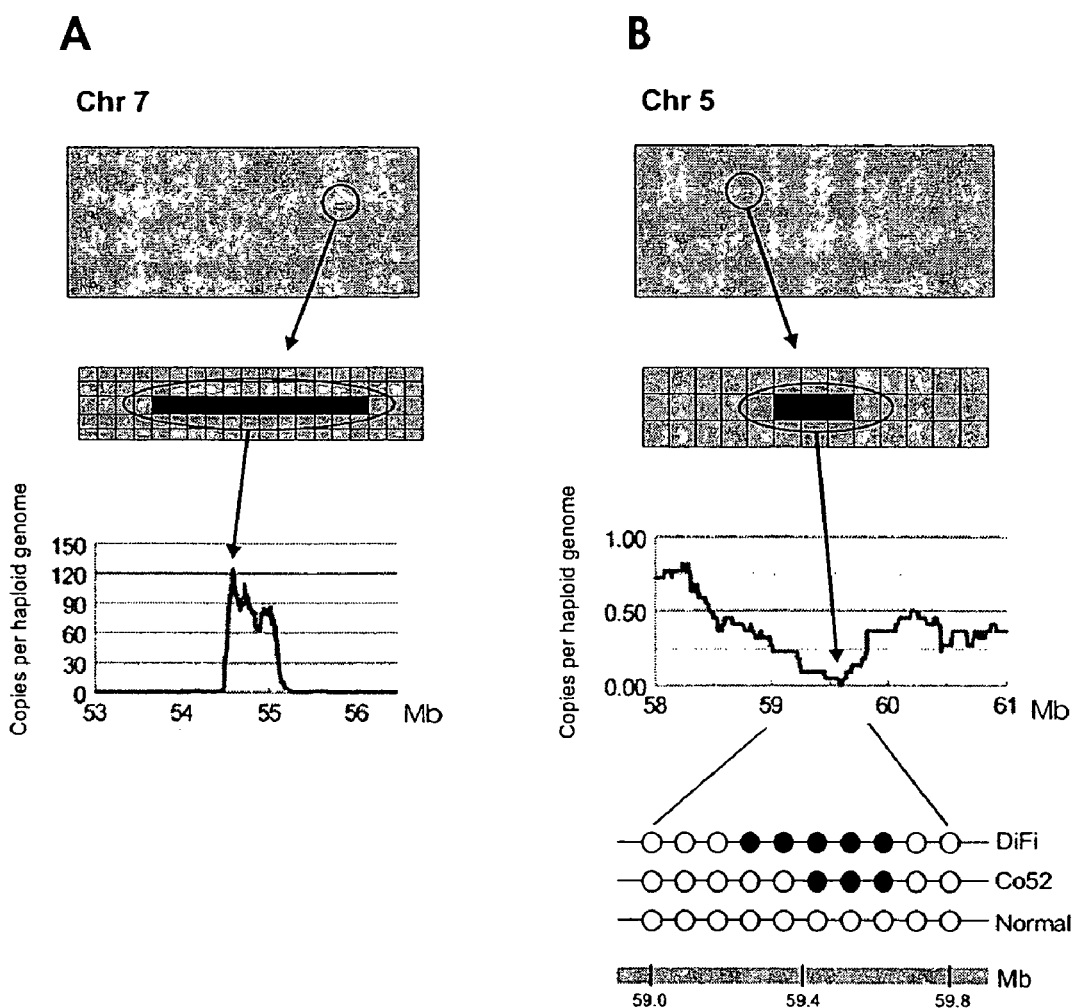
FIGS. 3A and 3B. High resolution tag density maps identify amplifications and deletions.

To identify amplifications, which typically involve regions much smaller than a chromosomal arm, average tag densities were dynamically calculated and visualized over sliding windows of different sizes. Although some relatively small alterations could be detected using a 1000 virtual tag window (FIG. 2), a window size of 50 virtual tags (~200 kb) was used for detailed analyses of amplifications because it would be expected to provide a relatively high resolution and sensitivity for experimental data consisting of ~100,000 filtered tags (Table 1). To visualize small alterations, we designed a bit-map based viewer that allowed much higher resolution views than possible with the standard chromosome maps such as commonly used for CGH. Using this strategy, three amplification events were observed in the DiFi genome, while none was observed in the lymphoblastoid DNA (Table 3). The most striking was a 125-fold amplification located at position 54.54-55.09 Mb on chromosome 7p (FIG. 3A). Analysis of tags in this area resolved the boundaries of the amplified region to within 10 kb. Three genes were harbored within the amplicon—a predicted gene with no known function (DKFZP564K0822), the bacterial lantibiotic synthetase component C-like 2 (LANCL2) gene, and the epidermal growth factor receptor (EGFR) gene, an oncogenic tyrosine kinase receptor known to be amplified in DiFi cells (23). The second highest amplification was a 6-fold change at position 30.36-32.72 Mb on chromosome 13 (FIG. 2). This area, containing 8 genes, represents the apex of a broad region on 13q that is co-amplified. Finally, a <300 kb region within 2 Mb of the telomere of chromosome 20q appeared to be increased >5 fold. Independent evaluation of the 7p, 13q and 20q amplified regions using quantitative PCR analyses of genomic DNA from DiFi cells revealed copy number gains similar to those observed by Digital Karyotyping (Table 3). CGH underestimated the fold amplification on 13q (FIG. 2). More importantly, CGH completely failed to identify the amplifications of chromosome 7p and 20q because the <0.5 Mb amplicons were below the level of resolution achievable with this technique.

TABLE 3

Quantitative analysis of amplifications and deletions

| Type of Alteration | Location | Copy number* (Digital Karyotyping) | Copy number* (quantitative PCR) |
|---|---|---|---|
| Amplifications | Chr 7: 54.54-55.09 Mb | 125 | 139 |
|  | Chr 13: 30.36-32.72 Mb | 6.4 | 5.7 |
|  | Chr 20: 60.54-60.83 Mb | 5.4 | 2.8 |
| Deletions | Chr 18: 49.34-51.67 Mb | 0 | 0 |
|  | Chr 5: 59.18-59.92 Mb | 0 | 0 |
|  | Chr X: 106.44-107.25 Mb | 0 | 0.4 |

*Copy number values are calculated per haploid genome as described in the Materials and Methods section.

Example 5

Analysis of Deletions

When a homozygous deletion occurs in a cancer cell, there are zero copies of the deleted sequences compared to two copies in normal cells. This difference is far less than that observed with amplifications, wherein 10-200 copies of the involved sequences are present in cancer cells compared to two copies in normal cells. Detection of homozygous deletions was therefore expected to be more difficult than the detection of amplifications. To assess the potential for detecting deletions, we first performed Digital Karyotyping on DNA from a cancer cell line (Hx48) known to have a homozygous deletion encompassing the SMAD4 and DCC genes on chromosome 18q (24). From a library of ~116,000 filtered tags, we were able to clearly identify this deletion on chromosome 18 (Table 3). The size of this deletion was estimated to be 2.33 Mb from Digital Karyotyping and 2.48 Mb from PCR-based analysis of markers in the region.

We next attempted to determine whether any deletions were present in DiFi cells. Using a window size of 150 virtual tags (600 kb), we found evidence for four homozygous deletions in the DiFi genome but none in the NLB cells. These apparent deletions were on chromosomes 4p, 5q, 16q, and Xq, and were of sizes 782 kb, 743 kb, 487 kb, and 814 kb, respectively. Assessment of the regions on 4p and 16q by quantitative PCR did not confirm the deletions, either because they were located between the markers used for PCR analyses or because there were no genuine homozygous deletions. This latter possibility was not unexpected given the positive predicted value (PPV) estimated for a window size of 150 Virtual Tags (Table 1), especially as the PPV value would be expected to be lower in an aneuploid genetic background. However, similar analyses did confirm the homozygous deletion at the 5q locus and showed a substantial reduction in genomic content at the chromosome X region in DiFi DNA (FIG. 3B; Table 3). Neither of these deletions was detected by conventional CGH analysis (FIG. 2). Further examination of the 5q locus by STS mapping demonstrated that the homozygous deletion was completely contained within the 59.18-59.92 Mb area identified by Digital Karyotyping and was ~450 kb in size (FIG. 3D). Analysis of 180 additional human colorectal tumors revealed an additional cell line (Co52) with a ~350 kb homozygous deletion of the same region, suggesting the existence of a novel tumor suppressor gene that may play a role in a subset of colorectal cancers.

Example 6

Detection of Foreign DNA Sequences

Figure 4:
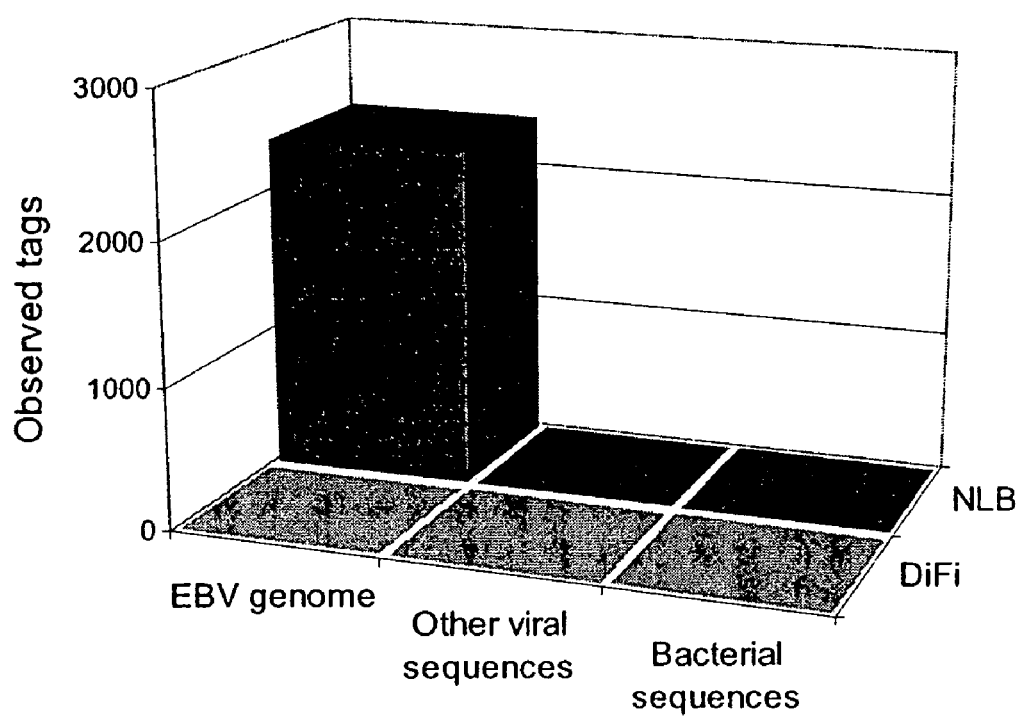
FIG. 4. Identification of EBV DNA in NLB cells. NLB, genomic tags derived from NLB cells after removal of tags matching human genome sequences or tags matching DiFi cells. DiFi, genomic tags derived from DiFi cells after removal of tags matching human genome sequences or tags matching NLB cells. The number of observed tags matching EBV, other viral, or bacterial sequences is indicated on the vertical axis.

Digital Karyotyping can in principle reveal sequences that are not normally present in human genomic DNA. The analysis of the library from NLB cells provided support for this conjecture. Like all lymphoblastoid lines, the NLB cells were generated through infection with Epstein-Barr virus (EBV) (25). EBV sequences persist in such lines in both episomal and integrated forms (26). To identify potential viral sequences in NLB cells, 210,245 unfiltered NLB tags were compared to virtual tags from the human genome and to unfiltered DiFi tags. These comparisons yielded a subset of tags that had no apparent matches to human genome and these were searched against virtual tags from all known viral or bacterial sequences. A total of 2368 tags perfectly matched EBV or EBV-related primate herpes viruses, but no tags matched other viral or bacterial sequences (FIG. 4). Of the 100 virtual tags predicted to be found in the EBV genome, 94 (94%) were found among the NLB tags. A similar analysis of 171,795 unfiltered DiFi tags showed no matches to EBV or other microbial sequences (FIG. 4)

Example 7

Materials and Methods

Digital Karotyping Library Construction

Digital Karyotyping was performed on DNA from colorectal cancer cell lines DiFi and Hx48, and from lymphoblastoid cells of a normal individual (GM12911, obtained from Coriell Cell Repositories, NJ). Genomic DNA was isolated using DNeasy or QIAamp DNA blood kits (Qiagen, Chatsworth, Calif.) using the manufacturers' protocols. For each sample 1 μg of genomic DNA was sequentially digested with mapping enzyme SacI, ligated to 20-40 ng of biotinylated linker (5'-biotin-TTTGCAGAGGTTCGTAATCGAGTTGGGT-GAGCT (SEQ ID NO: 1), 5'-phosphate-CACCCAACTC-GATTACGAACCTCTGC-3' (SEQ ID NO: 2)) (Integrated DNA Technologies, Coralville, Iowa) using T4 ligase (Invitrogen, Carlsbad, Calif.), and then digested with the fragmenting enzyme NlaIII. DNA fragments containing biotinylated linkers were isolated by binding to streptavidin coated magnetic beads (Dynal, Oslo, Norway). The remaining steps were similar to those described for LongSAGE of cDNA (18). In brief, linkers containing MmeI recognition sites were ligated to captured DNA fragments, and tags were released with MmeI (University of Gdansk Center for Technology Transfer, Gdansk, Poland and New England Biolabs, Beverly, Mass.). The tags were ligated to form ditags, and the ditags were isolated and then ligated to form concatemers which were cloned into pZero (Invitrogen, Carlsbad, Calif.). Sequencing of concatamer clones was performed using the Big Dye Terminator v3.0 Kit (Applied Biosystems) and analyzed with a SCE-9610 192—capillary electrophoresis system (Spectru-Medix, State College, Pa.) or by contract sequencing at Agencourt (Beverly, Mass.). Digital Karyotyping sequence files were trimmed using Pbred sequence analysis software (CodonCode, Mass.) and 21 bp genomic tags were extracted using the SAGE2000 software package, which identifies the fragmenting enzyme site between ditags, extracts intervening tags, and records them in a database. Detailed protocols for performing Digital Karyotyping and software for extraction and analysis of genomic tags are available at the http protocol, the sagenet.org domain name, and the digital_karyotyping-.htm path.

Simulations

The theoretical sensitivity and specificity of Digital Karyotyping for copy number alterations was evaluated using Monte Carlo simulations. For each alteration type, 100 simulations were performed as follows. Either 100,000 or 1,000,000 experimental tags were randomly assigned to 730,862 equally spaced virtual tags in a genome containing a single randomly placed copy number alteration of a predefined size and copy number. Moving windows containing the same number of virtual tags as the simulated alteration were used to evaluate tag densities along the genome. Tag density values of >4.9, <0.1, <0.6, and >1.4 located within the area of amplifications, homozygous deletions, heterozygous losses and subchromosomal gains, respectively, were considered true positives. Tag densities of these values in areas outside the altered region were considered false positives.

Data Analysis

All tags adjacent to the N/aIII fragmenting enzyme (CATG) sites closest to SacI mapping enzyme sites were computationally extracted from the human genome sequence (UCSC Jun. 28, 2002 Assembly, the http protocol, the genome.ucsc.edu domain name). Of the 1,094,480 extracted tags, 730,862 were obtained from unique loci in the genome and were termed virtual tags. The experimentally derived genomic tags obtained from NLB, DiFi and Hx48 cells were electronically matched to these virtual tags. The experimental tags with the same sequence as virtual tags were termed filtered tags arid were used for subsequent analysis. The remaining tags corresponded to repeated regions, sequences not present in the current genome database release, polymorphisms at the tag site, or sequencing errors in the tags or in the genome sequence database. Tag densities for sliding windows containing N virtual tags were determined as the sum of experimental tags divided by the average number of experimental tags in similar sized windows throughout the genome. Tag densities were dynamically analyzed in windows ranging from 50 to 1000 virtual tags. For windows of 1000 virtual tags, DiFi tag densities were normalized to evaluated NLB tag densities in the same sliding windows to account for incomplete filtering of tags matching repetitive sequences, and visualized using tag density maps. For windows less than 1000 virtual tags, a bitmap viewer was developed that specifically identified tag densities above or below defined thresholds.

Genome content differences between DiFi and normal cells were determined by quantitative real-time PCR using an iCycler apparatus (Bio-Rad, Hercules, Calif.). DNA content was normalized to that of Line-1, a repetitive element for which copy numbers per haploid genome are similar among all human cells (normal or neoplastic). Copy number changes per haploid genome were calculated using the formula $2^{(N_t - N_{line}) - (D_t - D_{line})}$ where $N_t$ is the threshold cycle number observed for experimental primer in the normal DNA sample, $N_{line}$ is the threshold cycle number observed for Line-1 primer in the normal DNA sample, $D_t$ is the average threshold cycle number observed for the experimental primer in DiFi and $D_{line}$ is the average threshold cycle number observed for Line-1 primer in DiFi. Conditions for amplification were: one cycle of 94° C., 2 mm followed by 50 cycles of 94° C., 20 sec, 57° C., 20 sec, 70° C., 20 sec. Threshold cycle numbers were obtained using iCycler software v2.3. PCR reactions for each primer set were performed in triplicate and threshold cycle numbers were averaged. For analysis of homozygous deletions, presence or absence of PCR products was evaluated by gel electrophoresis. PCR primers were designed using Primer 3 the http protocol, the www-genome.wi.mit.edu domain name, the path cgi-bin/primer/primer3_www.cgi) to span a 100-200 bp non-repetitive region and were synthesized by GeneLink (Hawthorne, N.Y.). Primer sequences for each region analyzed in this study are included in Table 4.

TABLE 4

Primer sequences used for quantitative PCR anlysis.

| Primer Name | Forward Primer | Reverse Primer | Chromosome or Accession Number | Location* |
|---|---|---|---|---|
| Line-1 | AAAGCCGCTCAACTACATGG (SEQ ID NO: 3) | TGCTTTGAATGCGTCCCAGAG (SEQ ID NO: 20) | M80343 | 2721 |
| Chr7-C | AGGCTAGTCTTGAACTCCTGACCTT (SEQ ID NO: 4) | ACCCTCCGATCCAGTAATTCTACTC (SEQ ID NO: 21) | Chromosome 7 | 5497607 |
| Chr13-A | GAGCAGAGGCCAAGGGTGTG (SEQ ID NO: 5) | CTATAACCTGGCACCCAAATGG (SEQ ID NO: 22) | Chromosome 13 | 31963904 |
| Chr13-B | CCCCACAGCAGTCTCCAAGAG (SEQ ID NO: 6) | GCTGAGGTCTTTGGGACATGG (SEQ ID NO: 23) | Chromosome 13 | 32256751 |
| ChX-A | CATGACTTCAGGTGGTGCTAGAGA (SEQ ID NO: 7) | GTATGCGTATATGTGGCAATACTGC (SEQ ID NO: 24) | Chromosome X | 107127218 |
| Ch4-hCT1955219-E8 | TTCCACTGAAAGGCCACAG (SEQ ID NO: 8) | TGAACAAAATTAACTCAAATTGCTG (SEQ ID NO: 25) | Chromosome 4 | 96488613 |
| Ch16-hCT1951220-E5 | CCCTGGGGATCAAAATCAC (SEQ ID NO: 9) | AATGGACTTGCTCATGCTTTC (SEQ ID NO: 26) | Chromosome 16 | 69127944 |
| Ch5-hCT1657046 | CTGGAAGGCTGGCAGATG (SEQ ID NO: 10) | TTGCTCCTACCTGTGAATCTTG (SEQ ID NO: 27) | Chromosome 5 | 58988143 |
| Ch5HD5'P | TCTGAACCATGGAGTTACAGAATGA (SEQ ID NO: 11) | CAGTCACCTTTCTCTACTGCACAAA (SEQ ID NO: 28) | Chromosome 5 | 59100130 |
| Ch5HD5'N | CAGAAAGTCCTCTTGCTCTTTTACG (SEQ ID NO: 12) | TGTTTAGTGTCACTTGTTTCCCTGA (SEQ ID NO: 29) | Chromosome 5 | 59184713 |
| Ch5HD5'L | TTGTATATAACAGGACGCACAATGG (SEQ ID NO: 13) | GCAGACCCTTATTTTCAGGAGGTAT (SEQ ID NO: 30) | Chromosome 5 | 59287952 |
| Ch5HD5'J | GCTTTCAAAAGGGAGAGACAAGAAT (SEQ ID NO: 14) | CAAGGAGAGAAACTTATTCCCACTG (SEQ ID NO: 31) | Chromosome 5 | 59390229 |
| Ch5-hCT1645609EC | CTATCTTGTCCGGAGACTTTCATGT (SEQ ID NO: 15) | TGACTCTAGAAACCCCATTGTTCTC (SEQ ID NO: 32) | Chromosome 5 | 59432676 |
| Ch5HD5'G | TAACATATTGCGGGAATGAGTACCT (SEQ ID NO: 16) | AAATCTCGTCCCCTTTAGACTATGG (SEQ ID NO: 33) | Chromosome 5 | 59476551 |
| Ch5HD5'E | ATTGTCTGAAGATAGCTGGATTTGG (SEQ ID NO: 17) | CAAATATCCTAGCCTGAAAGAAGCA (SEQ ID NO: 34) | Chromosome 5 | 59570278 |
| Ch5HD5'D | ATCTGCTGCTGTTTTAAAGCATTTC (SEQ ID NO: 18) | CCTTGTTCAAGGCTTTTTATTTTCA (SEQ ID NO: 35) | Chromosome 5 | 59683856 |
| Ch5-hCT1643862 | TGACCCGAGAATATCCCATC (SEQ ID NO: 19) | TTCCGTTCATGTGGTGAATC (SEQ ID NO: 36) | Chromosome 5 | 59877326 |

*Indicates location of forward primer in bp. All products were <500 bp in size.

Karyotyping and Comparative Genomic Hybridization

CGH was performed as previously described (19), and hybridization data were analyzed with the Leica Microsystems imaging software. Karyotyping was performed using standard procedures.

Example 8

Digital Karyotyping Using BcgI

An alternative experimental design to amplify thousand of genomic fragments distributed randomly throughout the genome with a single set of PCR primers utilizes the restriction endonuclease BcgI. This experimental design can be used to identify novel SNPs as well characterize genomic alterations including deletions, amplifications and other copy number alterations.

BcgI restriction fragments can be easily isolated from genomic DNA and can be ligated to a defined set of linker on both ends. Amplification of the final product only requires one set of PCR primers. BcgI fragments contain sufficient information to identify the genomic location from which they were derived. Quantitation of individual experimental tags or groups of tags over defined regions (windows) can be used to identify regions of deletion, amplification or copy number alterations. In addition, because subsets of genomic BcgI restriction fragments are polymorphic, these fragments can be used to identify SNPs.

A BcgI fragment library was constructed as follows. Human genomic DNA from four individuals (2.5 μg each) were pooled (10 μg total) and digested with BcgI at 30° C. for 30 min. BcgI restriction fragments were isolated by differential precipitation (perchloride precipitation followed by ethanol precipitation). Two linkers were ligated on to the BcgI fragments at 16° C. overnight. The linkers used were as follows:

Linker A top strand:

5'-TTGGATTTGCTGGTGCAGTACAACTAG-GCTTAACGTCTCACTANN-3' SEQ ID NO: 37)

Linker A bottom strand:

5'-p-TAGTGAGACGTTAAGCCTAGTTGTACTG-CACCAGCAAATCC-3' (SEQ ID NO:38)

Linker B top strand:

5'-TTTTACCTTCTGCGAAGCAGTTCGTCAA-CATAGACGTCTCACTANN-3' (SEQ ID NO: 39)

Linker B bottom strand:

5'-p-TAGTGAGACGTCTATGTTGACGAACT-GCTTCGCAGAAGGTA-3' (SEQ ID NO: 40)

Ligation products were PCR amplified with primer A and primer B:

```
Pimer A:
5'-CTAGGCTTAACGTCTCACTAGG-3'    (SEQ ID NO: 41)

Primer B:
5'-TCAACATAGACGTCTCACTAGG-3'    (SEQ ID NO: 42)
```

The resulting 78 bp PCR products were gel-purified and digested with BsmBI at 56° C. for 1 hour. The digestion products were ligated at 16° C. for 30 min to form concatemers. Concatemers were size-selected and cloned into plasmid pZero-Kan.

The BcgI library of fragments was sequenced with BigDye M13F primer on ABI377.

Two thousand five hundred eighty-nine clones were sequenced, identifying 22,038 tags and 5,123 contigs (windows). The contigs were found at the following frequencies:

3,581 contigs appeared twice or less;
1,321 contigs appeared three to ten times;
221 contigs appeared eleven times or more.

We found a total of 98 SNPs (7.4%) possible SNP.

| | | |
|---|---|---|
| A/G or C/T | 46 | (46%) |
| 1-nt Deletion | 26 | (28%) |
| A/C or G/T | 12 | (12%) |
| A/T | 8 | (8%) |
| C/G | 6 | (6%) |

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

REFERENCES

1. Vogelstein, B. & Kinzler, K. W. (2002) *The genetic basis of human cancer* (McGraw-Hill Health Professions Division, New York).
2. Scriver, C. R., Beaudet, A. L., Sly W. S., Valle, D. (2001) *The metabolic and molecular bases of inherited disease* (McGraw-Hill Health Professions Division, New York).
3. Kallioniemi, A., Kallioniemi, O. P., Sudar, D., Rutovitz, D., Gray, J. W., Waldman, F. & Pinkel, D. (1992) *Science* 258, 818-21.
4. Lisitsyn, N., Lisitsyn, N. & Wigler, M. (1993) *Science* 259, 946-51.
5. Schrock, E., du Manoir, S., Veldman, T., Schoell, B., Wienberg, J., Ferguson-Smith, M. A., Ning, Y., Ledbetter, D. H., Bar-Am, I., Soenksen, D., Garini, Y. & Ried, T. (1996) *Science* 273, 494-7.
6. Speicher, M. R., Gwyn Ballard, S. & Ward, D. C. (1996) *Nat Genet* 12, 368-75.
7. Solinas-Toldo, S., Lampel, S., Stilgenbauer, S., Nickolenko, J., Benner, A., Dohner, H., Cremer, T. & Lichter, P. (1997) *Genes Chromosomes Cancer* 20, 399-407.
8. Pinkel, D., Segraves, R., Sudar, D., Clark, S., Poole, I., Kowbel, D., Collins, C., Kuo, W. L., Chen, C., Zhai, Y., Dairkee, S. H., Ljung, B. M., Gray, J. W. & Albertson, D. G. (1998) *Nat Genet* 20, 207-11.
9. Pollack, J. R., Perou, C. M., Alizadeh, A. A., Eisen, M. B., Pergamenschikov, A., Williams, C. F., Jeffrey, S. S., Botstein, D. & Brown, P. O. (1999) *Nat Genet* 23, 41-6.
10. Cai, W. W., Mao, J. H., Chow, C. W., Damani, S., Balmain, A. & Bradley, A. (2002) *Nat Biotechnol* 20, 393-6.
11. Knuutila, S., Bjorkqvist, A. M., Autio, K., Tarkkanen, M., Wolf, M., Monni, O., Szymanska, J., Larramendy, M. L., Tapper, J., Pere, H., El-Rifai, W., Hemmer, S., Wasenius, V. M., Vidgren, V. & Zhu, Y. (1998) *Am J Pathol* 152, 1107-23.
12. Knuutila, S., Aalto, Y., Autio, K., Bjorkqvist, A. M., El-Rifai, W., Hemmer, S., Huhta, T., Kettunen, E., Kiuru-Kuhlefelt, S., Larramendy, M. L., Lushnikova, T., Monni, O., Pere, H., Tapper, J., Tarkkanen, M., Varis, A., Wasenius, V. M., Wolf, M. & Zhu, Y. (1999) *Am J Pathol* 155, 683-94.

13. Carpenter, N. J. (2001) *Semin Pediatr Neurol* 8, 135-46.
14. Hodgson, G., Hager, J. H., Volik, S., Hariono, S., Wernick, M., Moore, D., Nowak, N., Albertson, D. G., Pinkel, D., Collins, C., Hanahan, D. & Gray, J. W. (2001) *Nat Genet* 29, 459-64.
15. Gray, J. W. & Collins, C. (2000) *Carcinogenesis* 21, 443-52.
16. Snijders, A. M., Nowak, N., Segraves, R., Blackwood, S., Brown, N., Conroy, J., Hamilton, G., Hindle, A. K., Huey, B., Kimura, K., Law, S., Myambo, K., Palmer, J., Ylstra, B., Yue, J. P., Gray, J. W., Jain, A. N., Pinkel, D. & Albertson, D. G. (2001) *Nat Genet* 29, 263-4.
17. Velculescu, V. E., Zhang, L., Vogelstein, B. & Kinzler, K. W. (1995) *Science* 270, 484-487.
18. Saha, S., Sparks, A. B., Rago, C., Akmaev, V., Wang, C. J., Vogelstein, B., Kinzler, K. W. & Velculescu, V. E. (2002) *Nat Biotechnol* 20, 508-12.
19. Speicher, M. R., Prescher, G., du Manoir, S., Jauch, A., Horsthemke, B., Bornfeld, N., Becher, R. & Cremer, T. (1994) *Cancer Res* 54, 3817-23.
20. Olive, M., Untawale, S., Coffey, R. J., Siciliano, M. J., Wildrick, D. M., Fritsche, H., Pathak, S., Cherry, L. M., Blick, M., Lointier, P. & et al. (1993) *In Vitro Cell Dev Biol* 29A, 239-48.
21. Kinzler, K. W., Nilbert, M. C., Vogelstein, B., Bryan, T. M., Levy, D. B., Smith, K. J., Preisinger, A. C., Hamilton, S. R., Hedge, P., Markham, A., Carlson, M., Joslyn, G., Groden, J., White, R., Miki, Y., Miyoshi, Y., Nishisho, I. & Nakamura, Y. (1991) *Science* 251, 1366-70.
22. Platzer, P., Upender, M. B., Wilson, K., Willis, J., Lutterbaugh, J., Nosrati, A., Willson, J. K., Mack, D., Ried, T. & Markowitz, S. (2002) *Cancer Res* 62, 1134-8.
23. Dolf, G., Meyn, R. E., Curley, D., Prather, N., Story, M. D., Boman, B. M., Siciliano, M. J. & Hewitt, R. R. (1991) *Genes Chromosomes Cancer* 3, 48-54.
24. Thiagalingam, S., Lengauer, C., Leach, F. S., Schutte, M., Hahn, S. A., Overhauser, J., Willson, J. K., Markowitz, S., Hamilton, S. R., Kern, S. E., Kinzler, K. W. & Vogelstein, B. (1996) *Nat Genet* 13, 343-6.
25. Pelloquin, F., Lamelin, J. P. & Lenoir, G. M. (1986) *In Vitro Cell Dev Biol* 22, 689-94.
26. Cho, M. S. & Tran, V. M. (1993) *Virology* 194, 838-42.

We claim:

1. A method of karyotyping a genome of a test eukaryotic cell, comprising:

sequencing a population of pieces of the genome of the test eukaryotic cell to provide nucleotide sequence of said pieces;

matching, in silico, pieces of the genome to genomic locations using the nucleotide sequence of said pieces;

counting the pieces within windows of a selected size throughout the genome to determine number of pieces as a function of genomic location, wherein each window comprises a plurality of genomically clustered pieces;

comparing the number of pieces enumerated within each window for the test eukaryotic cell to the average number of pieces in windows of the selected size throughout the genome to obtain piece densities per window, wherein the piece densities per window represent the karyotype of the genome of the test eukaryotic cell.

2. The method of claim 1 wherein the pieces within each of the windows map within 40 kb.

3. The method of claim 1 wherein the pieces within each of the windows map within 200 kb.

4. The method of claim 1 wherein the pieces within each of the windows map within 600 kb.

5. The method of claim 1 wherein the pieces within each of the windows map within 4 Mb.

6. The method of claim 1 wherein the pieces are defined by the presence of a BcgI restriction endonuclease recognition site which is flanked by 12 nucleotides on either end.

7. The method of claim 1 further comprising the steps of:
comparing piece densities per window for the test eukaryotic cell to piece densities of a reference eukaryotic cell; and
identifying aneuploidy if (a) pieces of one or more autosomes are determined to be present in the test eukaryotic cell relative to the reference eukaryotic cell at a ratio of 1.5 or greater or less than 0.7; or (b) pieces of one or more sex chromosomes in a male are determined to be present in the test eukaryotic cell relative to a reference male eukaryotic cell at a ratio of 1.5 or greater or less than 0.7; or (c) pieces of X chromosomes in a female are determined to be present in the test eukaryotic cell relative to a reference male eukaryotic cell at a ratio of 3 or greater or less than 1.5 or relative to a reference female eukaryotic cell at a ratio of 1.5 or greater or less than 0.7.

8. The method of claim 1 wherein pieces representing less than 15% of the genome of the eukaryotic cell are sequenced, matched, and counted.

9. A method of determining differences in copy number of portions of the genome of a test eukaryotic cell, comprising:
sequencing a population of pieces of the genome of the test eukaryotic cell to provide nucleotide sequence of said pieces;
matching, in silico, pieces of the genome to genomic locations using the nucleotide sequence of said pieces;
dynamically counting the pieces within a moving window of a selected size to determine number of pieces as a function of genomic location, wherein the window comprises a plurality of genomically clustered pieces;
comparing number of pieces enumerated within the window at a genomic location to an average number of pieces in windows of the selected size throughout the genome to obtain piece density per window, wherein a difference in piece density per window between windows reflects a difference in copy number between portions of the genome.

10. The method of claim 9 wherein the difference in copy number is due to gain or loss of a whole chromosome.

11. The method of claim 9 wherein the difference in copy number is due to a gain or loss of a chromosomal arm.

12. The method of claim 9 wherein the difference in copy number is due to an interstitial amplification.

13. The method of claim 9 wherein the difference in copy number is due to an interstitial deletion.

14. The method of claim 9 wherein the pieces within the window map within 40 kb.

15. The method of claim 9 wherein the pieces within the window map within 200 kb.

16. The method of claim 9 wherein the pieces within the window map within 600 kb.

17. The method of claim 9 wherein the pieces within the window map within 4 Mb.

18. The method of claim 9 wherein the pieces are defined by the presence of a BcgI restriction endonuclease recognition site which is flanked by 12 nucleotides on either end.

19. The method of claim 9 further comprising the steps of:
comparing piece densities per window for the test eukaryotic cell to piece densities of a reference eukaryotic cell; and
identifying aneuploidy if (a) pieces of one or more autosomes are determined to be present in the test eukaryotic cell relative to the reference eukaryotic cell at a ratio of 1.5 or greater or less than 0.7; or (b) pieces of one or more sex chromosomes in a male are determined to be present in the test eukaryotic cell relative to a reference male eukaryotic cell at a ratio of 1.5 or greater or less than 0.7; or (c) pieces of X chromosomes in a female are determined to be present in the test eukaryotic cell relative to a reference male eukaryotic cell at a ratio of 3 or greater or less than 1.5 or relative to a reference female eukaryotic cell at a ratio of 1.5 or greater or less than 0.7.

20. The method of claim 9 wherein pieces representing less than 15% of the genome of the eukaryotic cell are sequenced, matched, and dynamically counted.

21. The method of claim 1 or 9 wherein the sequencing is performed by automated nucleotide sequence determination.

22. The method of claim 1 or 9 wherein between 100,000 and 1,000,000 pieces are sequenced and matched.

23. The method of claim 1 or 9 further comprising the step of:
comparing piece densities per window for the test eukaryotic cell to piece densities of a reference eukaryotic cell.

24. The method of claim 1 or 9 wherein the selected size is less than or equal to 40 kb.

25. The method of claim 1 or 9 wherein the selected size is less than or equal to 200 kb.

26. The method of claim 1 or 9 wherein the selected size is less than or equal to 600 kb.

27. The method of claim 1 or 9 wherein the selected size is less than or equal to 4 Mb.

* * * * *

SEQUENCE LISTING

```
<160> NUMBER OF SEQ ID NOS: 42

<210> SEQ ID NO 1
<211> LENGTH: 33
<212> TYPE: DNA
<213> ORGANISM: Homo sapiens

<400> SEQUENCE: 1
tttgcagagg ttcgtaatcg agttgggtga gct                                    33

<210> SEQ ID NO 2
<211> LENGTH: 26
<212> TYPE: DNA
<213> ORGANISM: Homo sapiens

<400> SEQUENCE: 2
cacccaactc gattacgaac ctctgc                                            26

<210> SEQ ID NO 3
<211> LENGTH: 20
<212> TYPE: DNA
<213> ORGANISM: Homo sapiens

<400> SEQUENCE: 3
aaagccgctc aactacatgg                                                   20

<210> SEQ ID NO 4
<211> LENGTH: 25
<212> TYPE: DNA
<213> ORGANISM: Homo sapiens

<400> SEQUENCE: 4
aggctagtct tgaactcctg acctt                                             25

<210> SEQ ID NO 5
<211> LENGTH: 20
<212> TYPE: DNA
<213> ORGANISM: Homo sapiens
```

```
<400> SEQUENCE: 5
gagcagaggc caagggtgtg                                            20

<210> SEQ ID NO 6
<211> LENGTH: 21
<212> TYPE: DNA
<213> ORGANISM: Homo sapiens

<400> SEQUENCE: 6
ccccacagca gtctccaaga g                                          21

<210> SEQ ID NO 7
<211> LENGTH: 24
<212> TYPE: DNA
<213> ORGANISM: Homo sapiens

<400> SEQUENCE: 7
catgacttca ggtggtgcta gaga                                       24

<210> SEQ ID NO 8
<211> LENGTH: 19
<212> TYPE: DNA
<213> ORGANISM: Homo sapiens

<400> SEQUENCE: 8
ttccactgaa aggccacag                                             19

<210> SEQ ID NO 9
<211> LENGTH: 19
<212> TYPE: DNA
<213> ORGANISM: Homo sapiens

<400> SEQUENCE: 9
ccctggggat caaaatcac                                             19

<210> SEQ ID NO 10
<211> LENGTH: 18
<212> TYPE: DNA
<213> ORGANISM: Homo sapiens

<400> SEQUENCE: 10
ctggaaggct ggcagatg                                              18

<210> SEQ ID NO 11
<211> LENGTH: 25
<212> TYPE: DNA
<213> ORGANISM: Homo sapiens

<400> SEQUENCE: 11
tctgaaccat ggagttacag aatga                                      25

<210> SEQ ID NO 12
<211> LENGTH: 25
<212> TYPE: DNA
<213> ORGANISM: Homo sapiens

<400> SEQUENCE: 12
cagaaagtcc tcttgctctt ttacg                                      25

<210> SEQ ID NO 13
<211> LENGTH: 25
<212> TYPE: DNA
<213> ORGANISM: Homo sapiens
```

-continued

<400> SEQUENCE: 13
ttgtatataa caggacgcac aatgg    25

<210> SEQ ID NO 14
<211> LENGTH: 25
<212> TYPE: DNA
<213> ORGANISM: Homo sapiens

<400> SEQUENCE: 14
gctttcaaaa gggagagaca agaat    25

<210> SEQ ID NO 15
<211> LENGTH: 25
<212> TYPE: DNA
<213> ORGANISM: Homo sapiens

<400> SEQUENCE: 15
ctatcttgtc cggagacttt catgt    25

<210> SEQ ID NO 16
<211> LENGTH: 25
<212> TYPE: DNA
<213> ORGANISM: Homo sapiens

<400> SEQUENCE: 16
taacatattg cgggaatgag tacct    25

<210> SEQ ID NO 17
<211> LENGTH: 25
<212> TYPE: DNA
<213> ORGANISM: Homo sapiens

<400> SEQUENCE: 17
attgtctgaa gatagctgga tttgg    25

<210> SEQ ID NO 18
<211> LENGTH: 25
<212> TYPE: DNA
<213> ORGANISM: Homo sapiens

<400> SEQUENCE: 18
atctgctgct gttttaaagc atttc    25

<210> SEQ ID NO 19
<211> LENGTH: 20
<212> TYPE: DNA
<213> ORGANISM: Homo sapiens

<400> SEQUENCE: 19
tgacccgaga atatcccatc    20

<210> SEQ ID NO 20
<211> LENGTH: 21
<212> TYPE: DNA
<213> ORGANISM: Homo sapiens

<400> SEQUENCE: 20
tgctttgaat gcgtcccaga g    21

<210> SEQ ID NO 21
<211> LENGTH: 25
<212> TYPE: DNA

<210> SEQ ID NO 21
<211> LENGTH: 25
<212> TYPE: DNA
<213> ORGANISM: Homo sapiens

<400> SEQUENCE: 21
accctccgat ccagtaattc tactc                                    25

<210> SEQ ID NO 22
<211> LENGTH: 22
<212> TYPE: DNA
<213> ORGANISM: Homo sapiens

<400> SEQUENCE: 22
ctataacctg gcacccaaat gg                                       22

<210> SEQ ID NO 23
<211> LENGTH: 21
<212> TYPE: DNA
<213> ORGANISM: Homo sapiens

<400> SEQUENCE: 23
gctgaggtct ttgggacatg g                                        21

<210> SEQ ID NO 24
<211> LENGTH: 25
<212> TYPE: DNA
<213> ORGANISM: Homo sapiens

<400> SEQUENCE: 24
gtatgcgtat atgtggcaat actgc                                    25

<210> SEQ ID NO 25
<211> LENGTH: 25
<212> TYPE: DNA
<213> ORGANISM: Homo sapiens

<400> SEQUENCE: 25
tgaacaaaat taactcaaat tgctg                                    25

<210> SEQ ID NO 26
<211> LENGTH: 21
<212> TYPE: DNA
<213> ORGANISM: Homo sapiens

<400> SEQUENCE: 26
aatggacttg ctcatgcttt c                                        21

<210> SEQ ID NO 27
<211> LENGTH: 22
<212> TYPE: DNA
<213> ORGANISM: Homo sapiens

<400> SEQUENCE: 27
ttgctcctac ctgtgaatct tg                                       22

<210> SEQ ID NO 28
<211> LENGTH: 25
<212> TYPE: DNA
<213> ORGANISM: Homo sapiens

<400> SEQUENCE: 28
cagtcacctt tctctactgc acaaa                                    25

<210> SEQ ID NO 29
<211> LENGTH: 25

```
<212> TYPE: DNA
<213> ORGANISM: Homo sapiens

<400> SEQUENCE: 29
tgtttagtgt cacttgtttc cctga                                    25

<210> SEQ ID NO 30
<211> LENGTH: 25
<212> TYPE: DNA
<213> ORGANISM: Homo sapiens

<400> SEQUENCE: 30 gcagacccett attttcagga ggtat                                   25

<210> SEQ ID NO 31
<211> LENGTH: 25
<212> TYPE: DNA
<213> ORGANISM: Homo sapiens

<400> SEQUENCE: 31
caaggagaga aacttattcc cactg                                    25

<210> SEQ ID NO 32
<211> LENGTH: 25
<212> TYPE: DNA
<213> ORGANISM: Homo sapiens

<400> SEQUENCE: 32
tgactctaga aaccccattg ttctc                                    25

<210> SEQ ID NO 33
<211> LENGTH: 25
<212> TYPE: DNA
<213> ORGANISM: Homo sapiens

<400> SEQUENCE: 33
aaatctcgtc ccctttagac tatgg                                    25

<210> SEQ ID NO 34
<211> LENGTH: 25
<212> TYPE: DNA
<213> ORGANISM: Homo sapiens

<400> SEQUENCE: 34
caaatatcct agcctgaaag aagca                                    25

<210> SEQ ID NO 35
<211> LENGTH: 25
<212> TYPE: DNA
<213> ORGANISM: Homo sapiens

<400> SEQUENCE: 35
ccttgttcaa ggctttttat tttca                                    25

<210> SEQ ID NO 36
<211> LENGTH: 20
<212> TYPE: DNA
<213> ORGANISM: Homo sapiens

<400> SEQUENCE: 36
ttccgttcat gtggtgaatc                                          20

<210> SEQ ID NO 37
```

```
<211> LENGTH: 45
<212> TYPE: DNA
<213> ORGANISM: Homo sapiens
<220> FEATURE:
<221> NAME/KEY: misc_feature
<222> LOCATION: (1)...(45)
<223> OTHER INFORMATION: n = A,T,C or G

<400> SEQUENCE: 37
ttggatttgc tggtgcagta caactaggct taacgtctca ctann          45

<210> SEQ ID NO 38
<211> LENGTH: 41
<212> TYPE: DNA
<213> ORGANISM: Homo sapiens

<400> SEQUENCE: 38
tagtgagacg ttaagcctag ttgtactgca ccagcaaatc c              41

<210> SEQ ID NO 39
<211> LENGTH: 46
<212> TYPE: DNA
<213> ORGANISM: Homo sapiens
<220> FEATURE:
<221> NAME/KEY: misc_feature
<222> LOCATION: (1)...(46)
<223> OTHER INFORMATION: n = A,T,C or G

<400> SEQUENCE: 39
ttttaccttc tgcgaagcag ttcgtcaaca tagacgtctc actann         46

<210> SEQ ID NO 40
<211> LENGTH: 41
<212> TYPE: DNA
<213> ORGANISM: Homo sapiens

<400> SEQUENCE: 40
tagtgagacg tctatgttga cgaactgctt cgcagaaggt a              41

<210> SEQ ID NO 41
<211> LENGTH: 22
<212> TYPE: DNA
<213> ORGANISM: Homo sapiens

<400> SEQUENCE: 41
ctaggcttaa cgtctcacta gg                                   22

<210> SEQ ID NO 42
<211> LENGTH: 22
<212> TYPE: DNA
<213> ORGANISM: Homo sapiens

<400> SEQUENCE: 42
tcaacataga cgtctcacta gg                                   22
```